US006765000B2

(12) United States Patent
Bonner, Jr. et al.

(10) Patent No.: US 6,765,000 B2
(45) Date of Patent: Jul. 20, 2004

(54) TREATMENT FOR REACTIVE ARTHRITIS OR BURSITIS

(76) Inventors: Ernest L. Bonner, Jr., 1406 Park St., Suite 400, Alameda, CA (US) 94501; Robert Hines, 3637 Cape Center Dr., Fayetteville, NC (US) 28304

(*) Notice: Subject to any disclaimer, the term of this patent is extended or adjusted under 35 U.S.C. 154(b) by 0 days.

(21) Appl. No.: 10/271,117

(22) Filed: Oct. 15, 2002

(65) Prior Publication Data

US 2003/0055022 A1 Mar. 20, 2003

Related U.S. Application Data

(63) Continuation of application No. 09/510,704, filed on Feb. 22, 2000, now Pat. No. 6,465,473, which is a continuation-in-part of application No. 09/270,962, filed on Mar. 17, 1999, now Pat. No. 6,087,382.

(51) Int. Cl.$^7$ .................. A61K 31/65; A61K 31/519; A61K 31/415

(52) U.S. Cl. .................. 514/152; 514/154; 514/262.1; 514/398

(58) Field of Search ................. 514/152, 154, 514/262.1, 398

(56) References Cited

U.S. PATENT DOCUMENTS

| 5,972,389 A | * | 10/1999 | Shell et al. ............. 424/501 |
| 6,087,382 A | * | 7/2000 | Bonner, Jr. et al. ....... 514/356 |
| 6,093,414 A | * | 7/2000 | Capelli .................. 424/405 |
| 6,465,473 B1 | * | 10/2002 | Bonner, Jr. et al. ....... 514/262 |

* cited by examiner

Primary Examiner—Raymond Henley, III
(74) Attorney, Agent, or Firm—Brian Beverly

(57) ABSTRACT

A treatment for conditions in human beings associated with either or both reactive arthritis or bursitis comprising a combination of acyclovir, minocycline hydrochloride, and metronidazole. An alternate treatment comprises the combination of valacyclovir hydrochloride, minocycline hydrochloride, and metronidazole.

7 Claims, No Drawings

TREATMENT FOR REACTIVE ARTHRITIS OR BURSITIS

This is a continuation of application Ser. No. 09/510,704, filed Feb. 22, 2000, which is now U.S. Pat. No. 6,465,473, which was a continuation-in-part of application Ser. No. 09/270,962, filed Mar. 17, 1999, now U.S. Pat. No. 6,087,382.

BACKGROUND OF THE INVENTION

This invention relates to an improved pharmaceutical formulation treatment of symptoms associated in humans with reactive arthritis or idiopathic bursitis.

Reactive arthritis refers to a spondyloarthritity which usually arises as a complication of an infection elsewhere in the body. Reactive arthritis can be caused by species of Shigella bacteria (most notably *Shigella flexneri*), *Yersinia enterocolitica*, *Campylobacter jejuni*, several species of *Salmonella*, genitourinary pathogens, *Chlamydia trachomatis*, Neisseria gonorrhea, *Ureaplasma urealyticum*, *Streptococcus pyogenes*, and other yet unidentified infectious agents.

Reactive arthritis commonly occurs in young men and women, but can occur at any age. Sufferers experience joint pain, stiffness, redness or swelling. Common symptoms may include fatigue, malaise, fever, and weight loss. The joints of the lower extremities, including the knee, ankle, and joints of the foot, are the most common sites of involvement, but symptoms can also occur in the wrists, fingers, elbows, shoulders, neck, and lower back. Other symptoms may include urethritis and prostatitis in males, and cervicitis or salpingitis in females. Ocular disease is common ranging from transient, asymptomatic conjunctivitis to aggressive anterior uveitis that occasionally results in blindness. Mucocutaneous lesions and nail changes are frequent. On less frequent or rare occasions manifestations of reactive arthritis include cardiac conduction defects, aortic insufficiency, central or peripheral nervous system lesions, and pleuropulmonary infiltrates.

Treatment of patients suffering from reactive arthritis with nonsteroidal anti-inflammatory drugs ("NSAID") provides some benefit, although symptoms of reactive arthritis are rarely completely alleviated and some patients fail to respond at all. The preferred initial treatment of choice for acute reactive arthritis is indomethacin in divided doses of 75 to 150 milligrams per day. The NSAID of last resort is phenylbutazone, in doses of 100 milligrams twice or three times per day, because of its potentially serious side effects. Patients with debilitating symptoms refractory to NSAID therapy may be treated with cytotoxic agents such as azathioprine or methotrexate, or with sulfasalazine. Tendinitis, other lesions, and uveitis may benefit from corticosteroids. Minocycline hydrochloride, a semisynthetic derivative of tetracycline, is indicated for infections caused by at least Shigella microorganisms, Streptococcus pyogenes, and Neisserie gonorrhoeae. It is therefore an accepted treatment in incidents of reactive arthritis triggered by these biological entities.

Long-term follow-up studies have suggested that some joint symptoms persist in many, if not most, patients with reactive arthritis. Recurrences of the more acute symptoms are common and as many as twenty-five percent of patients either become unable to work or are forced to change occupations because of persistent joint problems.

Bursitis is inflammation of a bursa, a thin-walled sac lined with synovial tissue. The function of the bursa is to facilitate movement of tendons and muscles over bony prominences. Bursitis may be caused by excessive frictional forces, trauma, systemic disease such as rheumatoid arthritis or gout, or infection. The most common form of bursitis is subacromial. Trochanteric bursitis causes patients to experience pain over the lateral aspect of the hip and upper thigh, and tenderness over the posterior aspect of the greater trochanter. Retrocalcaneal bursitis involves the bursa located between the calcaneus and the posterior surface of the Achilles tendon. Pain is experienced at the back of the heel, and swelling appears on either or both of the medial and lateral sides of the tendon. Retrocalcaneal bursitis occurs in association with spondyloarthritities, rheumatoid arthritis, gout, and trauma.

Treatment of bursitis generally consists of prevention of the aggravating condition, rest of the involved part, an NSAID, and local steroid injection. In the long term, bursitis can result in loss of use of a joint and chronic pain syndrome.

The long term effects of reactive arthritis and bursitis range from chronic pain to crippling disability. It is also thought that many instances of osteoarthritis and psoriatic arthritis are in actuality reactive arthritis. Unfortunately, current procedures for management treat the symptoms of these diseases rather than their underlying pathogens.

SUMMARY OF THE INVENTION

The inventors have discovered that significant benefits can be obtained by treating humans affected with conditions associated with reactive arthritis or bursitis using combinations of acyclovir, minocycline hydrochloride, and metronidazole or, alternatively, valacyclovir hydrochloride, minocycline hydrochloride, and metronidazole.

Acyclovir is an anti-viral drug. The chemical name of acyclovir is 2-amino-1,9-dihydro-9[(2-hydroxyethoxy) methyl]-6H-purin-6-one. Acyclovir is commercially available under the brand name ZOVIRAX® in capsules, tablets, or suspension. Acyclovir has demonstrated anti-viral activity against herpes simplex virus types I and II, varicella-zoster virus, Epstein-Barr virus and cytomegalovirus, both in vitro and in vivo.

Valacyclovir hydrochloride (sold under the brand name Valtrex®) is the hydrochloride salt of L-valyl ester of acyclovir. The chemical name of valacyclovir hydrochloride is L-valine, 2-[(2-amino-1,6-dihydro-6-oxo-9H-purin-9-yl) methoxy]ethyl ester, monohydrochloride. Valacyclovir hydrochloride is rapidly and nearly completely converted to acyclovir in the body.

Minocycline hydrochloride is a bacteriostatic antibiotic which exerts its antimicrobial effect by inhibition of bacterial protein synthesis. It has been shown to be effective against gram-negative bacteria, some gram-positive bacteria and other microorganisms.

Metronidazole is an oral synthetic antiprotozoal and antibacterial agent. Heretofore it has been indicated for treatment of symptomatic trichomoniasis, intestinal amebiasis, and a wide range of intra-abdominal, skin, and gynecological, bone and joint, and lower respiratory tract and central nervous system infections, bacterial septicemia and endocarditis.

The preferred embodiment of a formulation for treatment of the symptoms in human beings of reactive arthritis or idiopathic bursitis, or both, comprises the combination of acyclovir, minocycline hydrochloride, and metronidazole. An alternative formulation comprises the substitution of valacyclovir hydrochloride in place of acyclovir. The pharmaceutical dosages of the compounds of the combination may be administered in capsules, tablets, in suspension form, or by injection.

The invention provides a pharmaceutical combination that puts the diseases of reactive arthritis and bursitis into remission. Treatment with the combination may effect a cure of reactive arthritis and bursitis, but definitive testing has not been performed to confirm that fact.

It is therefore a primary object of the invention to provide a combination for treating conditions in human beings associated with either or both reactive arthritis or idiopathic bursitis.

Another object of the invention is to provide a treatment for conditions in human beings associated with either or both reactive arthritis or idiopathic bursitis that puts the disease being treated into full remission.

A further object of the invention is to provide a treatment for any constellation of symptoms amenable to treatment using the above combination, including for example, cases of reactive arthritis which have been misdiagnosed as osteoarthritis or psoriatic arthritis.

A still further object of the invention is to provide a combination comprising a pharmaceutical carrier for treating conditions in human beings associated with either or both reactive arthritis or idiopathic bursitis.

DETAILED DESCRIPTION OF THE INVENTION

Application Ser. No. 09/270,962 describes a method of treatment involving administration of a combination of L-lysine, minocycline hydrochloride, and metronidazole. An alternate method includes administration of InH for those individuals who have tested positively for mycobacterial exposure, along with the underlying combination of L-lysine, minocycline hydrochloride, and metronidazole. Another method described in application Ser. No. 09/510, 704 includes administration of valacyclovir hydrochloride with the underlying combination of L-lysine, minocycline hydrochloride, and metronidazole. A third method of treatment, described in applicant's application Ser. No. 09/613,876, now U.S. Pat. No. 6,197,776, includes administration of acyclovir with the underlying combination of L-lysine, minocycline hydrochloride, and metronidazole. The preferred embodiment of the present treatment comprises a pharmaceutical formulation including acyclovir, minocycline hydrochloride, and metronidazole. Alternatively, the treatment may include valacyclovir hydrochloride, minocycline hydrochloride, and metronidazole. Either of these embodiments may be supplemented with administration of pyridoxine hydrochloride, glucosamine, manganese, vitamin C, and desalinated seawater, such as Essence of Life.

Administration will generally be accomplished orally via capsules, tablets, or in suspension form, but delivery could be accomplished by injection, or any other method commonly used for administration of internal medicines.

Like L-lysine, acyclovir inhibits herpes simplex viruses, but by a different mechanism. While L-lysine tends to stop the virus from replicating by inhibiting the initiation of the replication process, acyclovir inhibits effective replication of actively replicating viral particles by stopping replication of herpes viral DNA. This is accomplished by either competitive inhibition or inactivation of viral DNA polymerase or incorporation and termination of the growing viral DNA chain. In double-blind testing, it has been found that the administration of the combination of acyclovir, minocycline hydrochloride, and metronidazole is an effective treatment for reactive arthritis or bursitis. Acyclovir has never been used in the prior art for treatment of arthritis or bursitis. It does not appear to be effective alone for the treatment of these diseases. The daily dose of acyclovir may vary from 200 mg to 4 grams. The preferred dose of acyclovir is 400 mg twice daily.

The preferred dose of minocycline hydrochloride is an initial dosage of 200 mg followed by doses of 100 mg twice per day. Daily doses of minocycline hydrochloride following the initial administration of 200 mg may vary from 50 mg to 200 mg. Based upon their similar properties, it is expected that other members of the tetracycline family such as doxycycline can be effectively substituted, in the combination, for minocycline hydrochloride.

The preferred dose of metronidazole is 250–500 mg twice per day. The total dose per day of metronidazole may vary from 100 mg to 1,000 mg.

It is known that the combination of minocycline hydrochloride, InH, and metronidazole inhibits the multiplication of susceptible organisms, including shigella, salmonella, chlamydia, streptococci, and mycobacteria. Applicants have also determined that the combination of L-lysine, minocycline hydrochloride, and metronidazole provides a medically effective treatment for reactive arthritis and bursitis. See U.S. Pat. No. 6,087,382. It has also been shown that the combination of acyclovir, L-lysine, minocycline hydrochloride, and metronidazole provides an effective treatment for these conditions. See U.S. Pat. No. 6,197,776. Individuals with severe symptoms, including joint swelling and joint contractures, who were not thought to be candidates for treatment using the combination of L-lysine, minocycline hydrochloride, and metronidazole only, have also experienced substantial beneficial effects in response to treatment with that combination and valacyclovir hydrochloride.

The preferred embodiment of the present invention comprises the combination of acyclovir or its prodrug, valacyclovir, with minocycline hydrochloride and metronidazole. It is believed that acyclovir results in a substantial benefit due to its inhibition of virus replication. The total combination of medicines in each of these embodiments presents a broad spectrum approach that it is believed effectively addresses the underlying pathogenesis for reactive arthritis and what has previously been referred to as idiopathic bursitis, and further is a beneficial treatment for reactive arthritis in particular cases wherein the symptom complex has been misdiagnosed as osteoarthritis or psoriatic arthritis, or in any other similar cases of misdiagnosis.

EXAMPLES

The following examples serve to illustrate the invention, but are not meant to restrict its effective scope.

Example 1

A 54 year old male presented with joint pain in his neck, upper back, lower back, both shoulders, both elbows, both wrists, both hands, both hips, both ankles, both knees, and both Achilles tendons at insertion. This patient also had effusion in both knees. He was unable to run or jog, had extreme difficulty squatting, was unable to fully squat, and had difficulty arising from a sitting position. He was treated with acyclovir, 400 mg BID, minocycline hydrochloride, 100 mg BID, and metronidazole, 250 mg BID, for 8 weeks. The patient experienced resolution of joint tenderness at all mentioned joints, excepting the PIP joint of the third digit of his right hand and his left knee, though such tenderness had decreased in severity in both those joints; and resolution of knee effusions. Before treatment, this patient experienced stiffness in all aforementioned joints lasting for up to 18 hours daily. After treatment stiffness remained in only four joint for about 10 minutes daily.

Example 2

A female, 79 years old presented with tenderness in her left shoulder, right elbow, both hands, both knees, her right hip, both ankles, the Achilles insertion of both feet, her lower back, and both wrists. She also experienced effusion in both knees, and pretibial edema bilaterally. This individual had stiffness in her joints for about 4 hours a day. After treatment with acyclovir, 400 mg BID, minocycline hydrochloride, 100 mg BID, and metronidazole, 250 mg BID, for 8 weeks, tenderness remained in only the right ankle with a decrease in severity at that joint. Tenderness decreased in severity in each joint from "moderate to severe" before treatment, to "slight" post-treatment. The effusions and pretibial edema had resolved. The patient went from a semi-sedentary state to being able to walk around daily for 20 minutes at a time and was able to resume her shopping activities and performing household chores.

There have been thus described certain preferred embodiments of a pharmaceutical formulation for treatment of conditions in human beings associated with either or both reactive arthritis or idiopathic bursitis. While preferred embodiments have been described and disclosed, it will be recognized by those with skill in the art that modifications are within the true scope and spirit of the invention. The appended claims are intended to cover all such modifications.

We claim:

1. A pharmaceutical formulation for use in treating reactive arthritis or bursitis in a mammal, including a human, comprising:

an effective amount of the combination of a first dosage unit comprising acyclovir or a pharmaceutically acceptable ester thereof, a second dosage unit comprising a member of the tetracycline family, and a third dosage unit comprising metronidazole.

2. A pharmaceutical formulation comprising a combination according to claim 1 wherein:

said member of the tetracycline family comprises minocycline hydrochloride.

3. A pharmaceutical formulation comprising a combination according to claim 2 in association with one or more pharmaceutically acceptable carriers therefor.

4. A pharmaceutical formulation according to claim 2 suitable for oral administration.

5. A pharmaceutical formulation according to claim 3 wherein:

said first dosage unit of acyclovir is a dosage amount within the range of about 200 mg to 4 gm, said second dosage unit of minocycline hydrochloride is a dosage amount within the range of about 50–200 mg, and said third dosage unit of metronidazole is a dosage amount within the range of about 100–1,000 mg.

6. A pharmaceutical formulation according to claim 5 wherein:

said first dosage unit of acyclovir is a dosage amount of about 400 mg, said second dosage unit of minocycline hydrochloride is a dosage amount of about 100 mg, and said third dosage unit of metronidazole is a dosage amount of about 250 mg.

7. A pharmaceutical formulation comprising a combination according to claim 1 wherein:

said pharmaceutically acceptable ester of acyclovir comprises a pharmaceutically acceptable salt of said ester.

* * * * *